United States Patent
Le Devedec et al.

(10) Patent No.: US 11,998,632 B2
(45) Date of Patent: Jun. 4, 2024

(54) ORAL CANNABINOID COMPOSITIONS AND METHODS FOR TREATING NEUROPATHIC PAIN

(71) Applicant: Avicanna Inc., Toronto (CA)

(72) Inventors: Frantz Henri Emmanuel Le Devedec, North York (CA); Aras Azadian, Toronto (CA); Setu Nimish Purohit, Toronto (CA); Justin Michael Grant, Toronto (CA); Samantha Carolyn Watt, Toronto (CA)

(73) Assignee: Avicanna Inc., Toronto (CA)

(*) Notice: Subject to any disclaimer, the term of this patent is extended or adjusted under 35 U.S.C. 154(b) by 555 days.

(21) Appl. No.: 17/012,366

(22) Filed: Sep. 4, 2020

(65) Prior Publication Data

US 2021/0069103 A1   Mar. 11, 2021

Related U.S. Application Data

(60) Provisional application No. 62/896,408, filed on Sep. 5, 2019.

(51) Int. Cl.
*A61K 9/00* (2006.01)
*A61K 9/107* (2006.01)
*A61K 9/48* (2006.01)
*A61K 31/05* (2006.01)
*A61K 47/10* (2017.01)
*A61K 47/14* (2017.01)
*A61K 47/26* (2006.01)

(52) U.S. Cl.
CPC ............ *A61K 9/0053* (2013.01); *A61K 9/107* (2013.01); *A61K 9/4808* (2013.01); *A61K 31/05* (2013.01); *A61K 47/10* (2013.01); *A61K 47/14* (2013.01); *A61K 47/26* (2013.01)

(58) Field of Classification Search
None
See application file for complete search history.

(56) References Cited

FOREIGN PATENT DOCUMENTS

WO   WO-2019036243 A1 * 2/2019 ............... A23L 2/00

* cited by examiner

*Primary Examiner* — Michael Barker
(74) *Attorney, Agent, or Firm* — DLA PIPER LLP (US); Dennis J. Parad (57) ABSTRACT

Self-emulsifying drug delivery systems are provided for oral delivery of cannabinoids. The cannabinoids are dissolved in an oily medium (e.g. medium chain triglycerides) together with at least one surfactant to improve dissolution, stability, and bioavailability. Also provided are methods comprising uses of an oral cannabinoid compositions for the treatment of neuropathic pain in a subject.

7 Claims, 4 Drawing Sheets

ORAL CANNABINOID COMPOSITIONS AND METHODS FOR TREATING NEUROPATHIC PAIN

CROSS-REFERENCE TO RELATED APPLICATIONS

This application claims priority to U.S. Provisional Application Ser. No. 62/896,408, filed Sep. 5, 2019, the content of which is herein incorporated by reference in its entirety.

FIELD

The present disclosure relates to compositions for oral administration of one or more cannabinoids to patients and, more particularly, through self-emulsifying drug delivery systems (SEDDS).

BACKGROUND

Cannabis has long been used for medicinal and recreational purposes. The active components of cannabis, i.e. phytocannabinoids, are effective as a drug against nausea and vomiting which are common side-effects of anaesthetics, opioids analgesics, chemotherapy for cancer and highly active anti-retroviral therapy (HAART for HIV-AIDS). Cannabis has also been used for a long period of time as a drug for relieving chronic neurogenic/neuropathic pain that is caused by surgical operations and by several disorders. Other medical indications include multiple sclerosis, depression, migraine, fibromyalgia, Parkinson syndrome and Gilles de la Tourette syndrome. It is also useful as spasmolytic, appetite stimulating, palliative and anti-convulsant medication.

Smoking is the most prevalent mode of use of cannabis. Smoking is a less desirable mode of administration for drugs, including medical cannabis, since it has adverse effects on the lungs. Cannabis smoke carries more tar and other particulate matter as compared to tobacco and may be a cause of lung diseases including chronic obstructive pulmonary disease (COPD) and lung cancer. Furthermore, many patients find the act of smoking unappealing due to social constraints.

Another method frequently employed is vaporisation wherein the herb is heated to about 180° C., rather than burned so that harmful side-products are hardly formed. Additionally, the vapour may be cooled or further purified if desired before inhalation. Furthermore, the dosage is easily controlled by the patient since inhalation provides for a rapid onset and a fast delivery into the bloodstream. However, the use of a vaporiser is also not always convenient since it requires a place or spot where the patient can set up and use his or her vaporiser to undergo treatment. In this respect it is also time-consuming.

Oral administration is the easiest and most convenient route for non-invasive drug administration. However, due to the highly lipophilic nature of cannabinoids, they are soluble in lipids and some organic solvents while being substantially insoluble or only sparsely soluble in water. The poor water-solubility of cannabinoids results in major difficulties in formulation and presents a major challenge to consistent drug delivery.

Furthermore, when administered orally in the form of an oil solution or some kind of water and/or oil suspension or emulsion, lipophilic compounds usually show poor bioavailability. The bioavailability of a drug depends on several parameters, i.e., the physicochemical nature of the active compound, the dosage form, as well as physiological factors. The cannabinoid compounds, being hydrophobic in nature, show wetting difficulties and poor dissolution in the gastrointestinal region.

Oral compositions comprising synthetic THC, e.g. gelatine capsules and tablets, are also known in the art. Marinol® (active component is dronabinol) is a soft gelatine capsule comprising synthetic THC. The bioavailability of Marinol® after oral intake is only approximately 15%. Namisol® (active component is dronabinol) is a THC sublingual tablet (ultra pure extract from *Cannabis sativa*), which is claimed to have a rapid uptake through the sublingual mucosa. The problem is that the tablet has to be kept under the tongue for the time it takes to dissolve in the saliva. Cesamet® (active component is nabilone) is a capsule comprising the synthetic cannabinoid nabilone. It is said to have fewer undesired side effects than THC.

Sativex® comprises THC and CBD and is commercially available as a buccal mouth spray for multiple sclerosis and for the alleviation of pain. Each spray of Sativex® delivers a fixed dose of 2.7 mg THC and 2.5 mg CBD. It is reported to cause irritation of the oral mucosa (20-25% of the patients) and to have a bad taste because of the high ethanol content.

Accordingly, there is a need for developing oral formulations of cannabinoids with improved delivery and enhanced bioavailability by masking the unpleasant taste of these lipophilic cannabinoids.

Therefore, an object of the present disclosure is to provide a more optimized and improved delivery system for cannabinoids to meet the desired needs of the patients. It is still another object of the present disclosure to provide an oral dosage form which provides sufficient bioavailability of cannabinoids for the treatment of neuropathic pain.

SUMMARY

In one aspect, there is provided a Self Emulsifying Drug Delivery System, commonly known as SEDDS, suitable for oral administration. More particularly, the present disclosure is directed to pharmaceutical cannabinoid compositions suitable for oral administration, in form of emulsion pre-concentrates, comprising:
 a. a cannabinoid at 0.01-10% (w/w),
 b. a surfactant at 40-50% (w/w),
 c. an oil or semi-solid fat at 15-25% (w/w), and
 d. a co-solvent at 25-35% (w/w)
wherein the said oral cannabinoid compositions forms an in-situ oil-in-water emulsion upon contact with aqueous media such as gastrointestinal fluids.

In some embodiments of the oral cannabinoid compositions as described herein, the cannabinoid is cannabidiol (CBD), cannabidiolic acid (CBDA), cannabidivarin (CBDV), cannabigerol (CBG), cannabigervarin (CBGV), tetrahydrocannabivarin (THCV), tetrahydrocannabinol (THC), or any combination thereof.

In some embodiments of the oral cannabinoid compositions as described herein, the cannabinoid is cannabidiol (CBD).

In some embodiments of the oral cannabinoid compositions as described herein, the surfactant is Polysorbate 60 (Tween-60) or Polysorbate 80 (Tween-80).

In some embodiments of the oral cannabinoid compositions as described herein, the oil or semi-solid fat is a medium chain triglyceride oil (MCT oil) extracted from coconut oil.

In some embodiments of the oral cannabinoid compositions as described herein, the co-solvent is polyethylene glycol (PEG).

In some embodiments of the oral cannabinoid compositions as described herein, the compositions are emulsion pre-concentrates at the time of administration to a subject. The emulsion pre-concentrates are filled into single unit dosage forms such as capsules, drinking ampoules and dose cushions, or may alternatively be formed as other suitable dosage forms such as powder, granules, pellets, chewable soft pills and chewy-base lozenges.

In some embodiments of the oral cannabinoid compositions as described herein, the compositions are capsules.

In some embodiments of the oral cannabinoid compositions as described herein, the compositions remain stable for 2-3-month incubation at 40° C.

In some embodiments of the oral cannabinoid compositions as described herein, the compositions have strong bioavailability profile in in-vivo models with peak plasma levels of >1000 ng/ml at 1 hour.

In some embodiments of the oral cannabinoid compositions as described herein, the compositions rapidly dispersed into nanosized droplets in 30 minutes to 2 hours time.

In some embodiments of the oral cannabinoid compositions as described herein, the compositions have nanocarrier dispersion profile with droplet size of 30 to 400 nm.

In another aspect, there is provided use of the oral cannabinoid formulations described herein for the treatment of neuropathic pain condition in a subject.

In some embodiments of the use as described herein, the neuropathic pain condition is caused by alcoholism; amputation; cancer; carpal tunnel syndrome; chemotherapy; diabetes; facial nerve problems; HIV infection/AIDS; multiple myeloma; multiple sclerosis; nerve or spinal cord compression from herniated discs or from arthritis in the spine; shingles; spine surgery; syphilis; thyroid problems or vitamin B deficiency.

Other aspects, features, and embodiments of the present disclosure will become apparent to those of ordinary skill in the art upon review of the following description of specific embodiments in conjunction with the accompanying figures.

DETAILED DESCRIPTION

It has been discovered by the present inventors that the cannabinoid or combination of cannabinoids comprised in compositions provided herein, upon oral administration to a mammal showed strong bioavailability profile as compared to controlled compositions.

Compositions provided herein comprise the combination of a surfactant, an oil and a co-solvent, which are selected such that these ingredients not only improve the solubility of cannabinoids in the formulation, but they also enhance the degree and rate of cannabinoids absorption and dispersion in the systemic circulation.

Provided herein pharmaceutical cannabinoid compositions suitable for oral administration, in form of pre-concentrates which forms an in-situ oil-in-water emulsion upon contact with aqueous media such as gastrointestinal fluids.

Also provided herein is a Self-emulsifying drug delivery system (SEDDS) to enhance the bioavailability of lipophilic cannabinoid compounds to achieve better therapeutic efficacy.

Compositions provided herein may be useful for treating neuropathic pain in a subject.

Compositions provided herein can also be used in conjunction with available treatments of neuropathic pain.

Oral cannabinoid compositions provided herein exhibit excellent overall stability, dissolution and bioavailability profile.

"Cannabinoid" as used herein, is meant to include compounds which interact with the cannabinoid receptor and various cannabinoid mimetics, such as cannabidiol (CBD), cannabidiolic acid (CBDA), cannabidivarin (CBDV), cannabigerol (CBG), cannabigervarin (CBGV), tetrahydrocannabivarin (THCV) and tetrahydrocannabinol (THC).

"Phytocannabinoids" as used herein means cannabinoids extracted from Cannabis plant species including by the way of non-limiting example *Cannabis sativa, Cannabis indica* and *Cannabis ruderalis* and all resins, stalks, flowers, seeds and oils related thereto.

The term "active agent" is generally understood to mean an active pharmaceutical ingredient.

As used herein, the terms "active ingredient," "active pharmaceutical ingredient," or "active pharmaceutical agent" refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable free acids, free bases, salts, or esters.

The term "formulation" or "composition" as used herein refers to the active pharmaceutical ingredient, nutraceutical, nutritional, vitamin, or drug in combination with pharmaceutically acceptable excipients. This includes orally administrable formulations as well as formulations administrable by other means.

The term "excipient" herein means any substance, not itself an active agent, which may be used as a carrier or vehicle for delivery of an active agent to a subject or combined with an active agent to improve its handling or storage properties or to permit or facilitate formation of a dose unit of the compositions.

As used herein, the terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

The term "drug delivery system" refers to a formulation or device that delivers therapeutic agent(s) to desired body location(s) and/or provides timely release of therapeutic agent(s).

The term "self-emulsifying" or "self-emulsifying drug delivery system (SEDDS)" refers to isotropic mixtures of natural or synthetic oils, solid or liquid surfactants, or alternatively, one or more hydrophilic solvents and co-solvents/surfactants. The combination of a pharmaceutical oil and a surfactant can provide a formulation, which emulsifies and disperses rapidly in the gastrointestinal fluid. Upon mild agitation followed by dilution in aqueous media, these systems can form fine oil-in-water (o/w) emulsions with a very small droplet size.

The term "therapeutically effective amount" or "therapeutically and/or prophylactically effective amount" as used herein refers to an amount of compound or agent that is sufficient to elicit the required or desired therapeutic and/or prophylactic response, as the particular treatment context may require. It will be understood that a therapeutically and/or prophylactically effective amount of an active agent for a subject is dependent inter alia on the body weight of the subject as well as other factors known to a person of ordinary skill in the art.

The terms "treat," "treating," or "treatment of" are used herein in their broad senses unless otherwise specifically indicated in the particular context, and results of a treatment may generally include reversing, alleviating, or inhibiting the progress of an indicated disorder or condition, or one or more symptoms of the disorder or condition.

"wt %" or "w/w %" when referring to the percentage of a component in a composition is percentage of the weight of the component in the composition relative to the total weight of the composition.

"Alleviate" as used herein, is meant to include complete elimination as well as any clinically or quantitatively measurable reduction in the subject's symptoms and/or discomfort.

A "subject" herein to which a therapeutic agent or compositions thereof can be administered includes mammals such as a human subject of either sex and of any age, and also includes any nonhuman animal, particularly a domestic or companion animal such as a cat, dog or horse, as well as laboratory animals such as rats or guinea pigs.

As used herein, the term "bioavailability" refers to the proportion of an active pharmaceutical ingredient that enters the systemic circulation when introduced into the body and is able to have a physiological effect.

As used herein, the term "enhanced bioavailability" refers to the increased proportion of an active pharmaceutical ingredient that enters the systemic circulation when introduced into the body as compared to a reference's bioavailability.

The term "stable compositions(s)" as used herein, refers to a compositions that does not show any precipitation in Fasted-State Simulated Gastric Fluid (FaSSGF) at pH 2.0, temperature of 37° C.±0.5° C. and under stirring at a speed of 50 rpm at least for 60 minutes. Also the term "stable compositions(s)" refers to a compositions which upon subjected to stability evaluation at 40° C. and 75% RH (relative humidity) or 25° C. and 60% RH (relative humidity), is substantially free of impurities, or comprises not more than 5% impurities, or comprises impurities levels which are acceptable by regulatory bodies such as US FDA.

As used herein, the term "dissolution rate" or "dispersion rate" refers to the amount of time it takes for an active ingredient (e.g. cannabidiol) or compositions thereof to dissolve in a solvent. The dissolution rate may depend on a variety of factors including mixing, temperature, pH, solvent, particle size, etc. The dissolution rate of a drug or compositions thereof affects the bioavailability of the drug. In certain circumstances, dissolution rate is used to determine drug availability from solid dosage forms.

As used herein, the terms "droplet size" and "particle size" both refer to the diameter of the respective droplet or particle, unless otherwise specifically noted.

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, neuropathic cancer pain, HIV/AIDS induced pain, phantom limb pain, and complex regional pain syndrome. Unless otherwise specified, the term also encompasses the common clinical features of neuropathic pain including, but not limited to, sensory loss, allodynia (non-noxious stimuli produce pain), hyperalgesia and hyperpathia (delayed perception, summation, and painful after sensation).

The term "efficacy" refers to the effectiveness of a particular active agent for its intended purpose, i.e., the ability of a given active agent to cause its desired pharmacologic effect.

The term "safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

The terms "tolerable" and "tolerability" refer to the ability of the pharmaceutical compositions of the present disclosure to not elicit an adverse reaction in the subject to whom such compositions is administered, or alternatively not to elicit a serious adverse reaction in the subject to whom such compositions is administered.

As discussed in greater detail in the illustrative and non-limiting examples provided herein, the present disclosure is directed to topical, formulations/compositions that incorporate at least one cannabinoid.

In one aspect, there are provided oral cannabinoid compositions comprising:
  a. a cannabinoid at 0.01-10% (w/w),
  b. a surfactant at 40-50% (w/w),
  c. an oil or semi-solid fat at 15-25% (w/w), and
  d. a co-solvent at 25-35% (w/w).
wherein the said oral cannabinoid compositions forms an in-situ oil-in-water emulsion upon contact with aqueous media such as gastrointestinal fluids.

Exemplary cannabinoids include cannabidiol (CBD), cannabidiolic acid (CBDA), cannabidivarin (CBDV), cannabigerol (CBG), cannabigervarin (CBGV), tetrahydrocannabivarin (THCV), tetrahydrocannabinol (THC), combinations, and mixtures thereof extracted from Cannabis plant species including *Cannabis sativa, Cannabis indica* and *Cannabis ruderalis* and all resins, stalks, flowers, seeds and oils related thereto.

In some exemplary, non-limiting embodiments, oral cannabinoid compositions provided herein may include about 0.01% to about 10% (w/w) of cannabinoid(s). For example, oral cannabinoid compositions provided herein may comprise about 0.01% to about 10%, 0.1% to about 10%, about 0.5% to about 10%, about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 0.01% to about 9%, about 0.1% to about 9%, about 0.5% to about 9%, about 1% to about 9%, about 2% to about 9%, about 3% to about 9%, about 4% to about 9%, about 5% to about 9%, about 6% to about 9%, about 7% to about 9%, about 8% to about 9%, about 0.01% to about 8%, about 0.1% to about 8%, about 0.5% to about 8%, about 1% to about 8%, about 2% to about 8%, about 3% to about 8%, about 4% to about 8%, about 5% to about 8%, about 6% to about 8%, about 7% to about 8%, about 0.01% to about 7%, about 0.1% to about 7%, about 0.5% to about 7%, about 1% to about 7%, about 2% to about 7%, about 3% to about 7%, about 4% to about 7%, about 5% to about 7%, about 6% to about 7%, about 0.01% to about 6%, about 0.1% to about 6%, about 0.5% to about 6%, about 1% to about 6%, about 2% to about 6%, about 3% to about 6%, about 4% to about 6%, about 5% to about 6%, about 0.01% to about 5%, about 0.1% to about 5%, about 0.5% to about 5%, about 1% to about 5%, about 2% to about 5%, about 3% to about 5%, about 4% to about 5%, about 0.01% to about 4%, about 0.1% to about 4%, about 0.5% to about 4%, about 1% to about 4%, about 2% to about 4%, about 3% to about 4%, about 0.01% to about 3%, about 0.1% to about 3%, about 0.5% to about 3%, about 1% to about 3%, about 2% to about 3%, about 0.01% to about 2%, about 0.1% to about 2%, about 0.5% to about 2%, about 1% to about 2%, about 0.01% to about 1%, about 0.1% to about 1%, about 0.5% to about 1%, about 0.01% to about 0.5%, about 0.1% to about 0.5% or about 0.01% to about 0.1% (w/w) of cannabinoid(s).

In some exemplary, non-limiting embodiments, oral cannabinoid compositions provided herein may comprise at least 0.01%, at least 0.1%, at least 0.5%, at least 1%, at least 2%, at least 3%, at least 4%, at least 5%, at least 6%, at least 7%, at least 8%, at least 9% or at least 10% (w/w) of cannabinoid(s).

In some exemplary, non-limiting embodiments, oral cannabinoid compositions provided herein may comprise about 0.01%, about 0.1%, about 0.5%, about 1%, about 2%, about 3%, about 4%, about 5%, about 6%, about 7%, about 8%, about 9% or about 10% (w/w) of cannabinoid(s).

In some exemplary, non-limiting embodiments, oral cannabinoid compositions provided herein may form emulsion pre-concentrates at the time of administration to a subject. The emulsion pre-concentrates may be filled into single unit dosage forms such as capsules, drinking ampoules and dose cushions, or may alternatively be formed as other suitable dosage forms such as powder, granules, pellets, chewable soft pills and chewy-base lozenges.

In some exemplary, non-limiting embodiments, cannabinoid compositions provided herein may be provided as oral self-emulsifying capsules.

Without being limited by any particular theory, it is expected that cannabinoid compositions provided herein enhance the proportion of cannabinoids in systemic circulation when introduced into the body through self-emulsification and are able to produce a physiological effect.

Other ingredients may be provided in oral cannabinoid compositions provided herein, so long as they are physiologically acceptable and suitable for use in combination with cannabinoids.

In some exemplary, non-limiting embodiments, oral cannabinoid compositions provided herein may include one or more surfactants, such as an ethoxylated fatty alcohol, polyethylene glycol (PEG) 1000 monocetyl ether, alkyl trimethyl ammonium bromide, glycerol monostearate, potassium stearate, sodium lauryl sulphate, sodium cetearyl sulphate, saponin, Polysorbate 20 (Tween 20), Polysorbate 40 (Tween 40), Polysorbate 60 (Tween 60) and Polysorbate 80 (Tween 80), combinations and mixtures thereof.

In some exemplary, non-limiting embodiments, oral cannabinoid compositions provided herein may include about 40% to about 50% (w/w) of surfactant(s). For example, oral cannabinoid compositions provided herein may comprise about 40% to about 50%, about 41% to about 50%, about 42% to about 50%, about 43% to about 50%, about 44% to about 50%, about 45% to about 50%, about 46% to about 50%, about 47% to about 50%, about 48% to about 50%, about 49% to about 50%, about 40% to about 49%, about 41% to about 49%, about 42% to about 49%, about 43% to about 49%, about 44% to about 49%, about 45% to about 49%, about 46% to about 49%, about 47% to about 49%, about 48% to about 49%, about 40% to about 48%, about 41% to about 48%, about 42% to about 48%, about 43% to about 48%, about 44% to about 48%, about 45% to about 48%, about 46% to about 48%, about 47% to about 48%, about 40% to about 47%, about 41% to about 47%, about 42% to about 47%, about 43% to about 47%, about 44% to about 47%, about 45% to about 47%, about 46% to about 47%, about 40% to about 46%, about 41% to about 46%, about 42% to about 46%, about 43% to about 46%, about 44% to about 46%, about 45% to about 46%, about 40% to about 45%, about 41% to about 45%, about 42% to about 45%, about 43% to about 45%, about 44% to about 45%, about 40% to about 44%, about 41% to about 44%, about 42% to about 44%, about 43% to about 44%, about 40% to about 43%, about 41% to about 43%, about 42% to about 43%, about 40% to about 42%, about 41% to about 42% or about 40% to about 41% (w/w) of surfactant(s).

In some exemplary, non-limiting embodiments, oral cannabinoid compositions provided herein may comprise at least 40%, at least 41%, at least 42%, at least 43%, at least 44%, at least 45%, at least 46%, at least 47%, at least 48%, at least 49% or at least 50% (w/w) of surfactant(s).

In some exemplary, non-limiting embodiments, oral cannabinoid compositions provided herein may comprise about 40%, about 41%, about 42%, about 43%, about 44%, about 45%, about 46%, about 47%, about 48%, about 49% or about 50% (w/w) of surfactant(s).

In some exemplary, non-limiting embodiments, oral cannabinoid compositions provided herein may include one or more oil(s) or semi-solid fat(s), which may comprise a variety of different oils e.g. soybean oil, olive oil, fish oil, fish oil extract, safflower oil, corn oil, sunflower oil, coconut oil, palm kernel oil, rapeseed oil, sesame oil, vegetable oils, mineral oils, medium chain triglycerides (MCT) and mixtures thereof.

In some exemplary, non-limiting embodiments, oral cannabinoid compositions provided herein may include about 15% to about 25% (w/w) of oil(s) or semi-solid fat(s). For example, oral cannabinoid compositions provided herein may comprise about 15% to about 25%, about 16% to about 25%, about 17% to about 25%, about 18% to about 25%, about 19% to about 25%, about 20% to about 25%, about 21% to about 25%, about 22% to about 25%, about 23% to about 25%, about 24% to about 25%, about 15% to about 24%, about 16% to about 24%, about 17% to about 24%, about 18% to about 24%, about 19% to about 24%, about 20% to about 24%, about 21% to about 24%, about 22% to about 24%, about 23% to about 24%, about 15% to about 23%, about 16% to about 23%, about 17% to about 23%, about 18% to about 23%, about 19% to about 23%, about 20% to about 23%, about 21% to about 23%, about 22% to about 23%, about 15% to about 22%, about 16% to about 22%, about 17% to about 22%, about 18% to about 22%, about 19% to about 22%, about 20% to about 22%, about 21% to about 22%, about 15% to about 21%, about 16% to about 21%, about 17% to about 21%, about 18% to about 21%, about 19% to about 21%, about 20% to about 21%, about 15% to about 20%, about 16% to about 20%, about 17% to about 20%, about 18% to about 20%, about 19% to about 20%, about 15% to about 19%, about 16% to about 19%, about 17% to about 19%, about 18% to about 19%, about 15% to about 18%, about 16% to about 18%, about 17% to about 18%, about 15% to about 17%, about 16% to about 17% or about 15% to about 16% (w/w) of oil(s) or semi-solid fat(s).

In some exemplary, non-limiting embodiments, oral cannabinoid compositions provided herein may comprise at least 15%, at least 16%, at least 17%, at least 18%, at least 19%, at least 20%, at least 21%, at least 22%, at least 23%, at least 24% or at least 25% (w/w) of oil(s) or semi-solid fat(s).

In some exemplary, non-limiting embodiments, oral cannabinoid compositions provided herein may comprise about 15%, about 16%, about 17%, about 18%, about 19%, about 20%, about 21%, about 22%, about 23%, about 24% or about 25% (w/w) of oil(s) or semi-solid fat(s).

In some exemplary, non-limiting embodiments, oral cannabinoid compositions provided herein may further comprise a pharmaceutically acceptable co-solvent.

In some exemplary, non-limiting embodiments, the co-solvent may be selected from the group consisting of diethylene glycol ethyl ether, methoxy polyethylene glycol, propylene glycol, polypropylene glycol, polyethylene glycol (PEG), glycerol, ethanol, dimethyl isosorbide, glycofurol, propylene carbonate, dimethyl acetamide, combinations or mixtures thereof.

The co-solvent preferably has a mean molecular weight in the range from 2000 to 20000 Da.

Preferably, the co-solvent is selected from the group consisting of PEG 2000, PEG 3000, PEG 4000, PEG 5000, PEG 6000, PEG 8000, PEG 10000 and PEG 20000.

In some exemplary, non-limiting embodiments, oral cannabinoid compositions provided herein may include about 25% to about 35% (w/w) of one or more co-solvent(s). For example, oral cannabinoid compositions provided herein may comprise about 25% to about 35%, about 26% to about 35%, about 27% to about 35%, about 28% to about 35%, about 29% to about 35%, about 30% to about 35%, about 31% to about 35%, about 32% to about 35%, about 33% to about 35%, about 34% to about 35%, about 25% to about 34%, about 26% to about 34%, about 27% to about 34%, about 28% to about 34%, about 29% to about 34%, about 30% to about 34%, about 31% to about 34%, about 32% to about 34%, about 33% to about 34%, about 25% to about 33%, about 26% to about 33%, about 27% to about 33%, about 28% to about 33%, about 29% to about 33%, about 30% to about 33%, about 31% to about 33%, about 32% to about 33%, about 25% to about 32%, about 26% to about 32%, about 27% to about 32%, about 28% to about 32%, about 29% to about 32%, about 30% to about 32%, about 31% to about 32%, about 25% to about 31%, about 26% to about 31%, about 27% to about 31%, about 28% to about 31%, about 29% to about 31%, about 30% to about 31%, about 25% to about 30%, about 26% to about 30%, about 27% to about 30%, about 28% to about 30%, about 29% to about 30%, about 25% to about 29%, about 26% to about 29%, about 27% to about 29%, about 28% to about 29%, about 25% to about 28%, about 26% to about 28%, about 27% to about 28%, about 25% to about 27% or about 25% to about 26% (w/w) of oil(s) or semi-solid fat(s).

In some exemplary, non-limiting embodiments, oral cannabinoid compositions provided herein may comprise at least 25%, at least 26%, at least 27%, at least 28%, at least 29%, at least 30%, at least 31%, at least 32%, at least 33%, at least 34% or at least 35% (w/w) of oil(s) or semi-solid fat(s).

In some exemplary, non-limiting embodiments, an oral cannabinoid compositions provided herein may comprise about 25%, about 26%, about 27%, about 28%, about 29%, about 30%, about 31%, about 32%, about 33%, about 34% or about 35% (w/w) of oil(s) or semi-solid fat(s).

In some exemplary, non-limiting embodiments, oral cannabinoid compositions provided herein may remain stable for 2-3 months from 0 to 40° C.

In some exemplary, non-limiting embodiments, oral cannabinoid compositions provided herein may have strong bioavailability profile in in-vivo models with peak plasma levels of about 900 to about 1100 ng/ml at 1 hour.

In some exemplary, non-limiting embodiments, oral cannabinoid compositions provided herein may dispersed into nanosized droplets in 30 minutes to 2 hours time after administration.

In some exemplary, non-limiting embodiments, oral cannabinoid compositions provided herein may have nanocarrier dispersion profile with droplet size of about 30 to about 400 nm as determined by dynamic light scattering.

It is understood that the amount of cannabinoid necessary to achieve a desired therapeutic result is influenced by, and will therefore vary based on, a number of factors, including for example and without limitation, the age, sex, and weight of the subject, factors that influence the metabolic rate, and the specific conditions, diseases or related treatment symptoms of the subject. The concentration of at least one cannabinoid in compositions provided herein is between about 0.01% and about 10% (w/w).

One of skill in the art will understand that the ingredients in the final formulations must total 100% and, based on the teachings provided herein, will understand that modifications to the exemplary formulations provided herein are possible (e.g., replacement of a recited ingredient with a different ingredient, addition of a different ingredient, and/or modification of an amount of an ingredient) provided that such modifications result in a formulation as taught and described herein (i.e. capable of delivering an active agent such a cannabinoid to the site of action).

In some exemplary, non-limiting embodiments, oral cannabinoid compositions may include cannabinoids in a specific therapeutic amount for treating neuropathic pain in a subject.

In some exemplary, non-limiting embodiments, the neuropathic pain in a subject is caused by but not limited to alcoholism; amputation; cancer; carpal tunnel syndrome; chemotherapy; diabetes; facial nerve problems; HIV infection/AIDS; multiple myeloma; multiple sclerosis; nerve or spinal cord compression from herniated discs or from arthritis in the spine; shingles; spine surgery; syphilis; thyroid problems or vitamin B deficiency.

The discussion herein and the following Examples set forth and illustrate various exemplary embodiments of the present disclosure, which are understood to be illustrative and non-limiting.

NON-LIMITING EMBODIMENTS

Particular embodiments of the disclosure include, without limitation, the following:

1. Oral cannabinoid compositions comprising:
   a. a cannabinoid at 0.01-10% (w/w),
   b. a surfactant at 40-50% (w/w),
   c. an oil or semi-solid fat at 15-25% (w/w), and
   d. a co-solvent at 25-35% (w/w).
2. The oral cannabinoid compositions of embodiment 1, which comprises about 0.01% (w/w) of the cannabinoid.
3. The oral cannabinoid compositions of embodiment 1, which comprises about 0.1% (w/w) of the cannabinoid.
4. The oral cannabinoid compositions of embodiment 1, which comprises about 0.5% (w/w) of the cannabinoid.
5. The oral cannabinoid compositions of embodiment 1, which comprises about 1% (w/w) of the cannabinoid.
6. The oral cannabinoid compositions of embodiment 1, which comprises about 2% (w/w) of the cannabinoid.
7. The oral cannabinoid compositions of embodiment 1, which comprises about 3% (w/w) of the cannabinoid.
8. The oral cannabinoid compositions of embodiment 1, which comprises about 4% (w/w) of the cannabinoid.
9. The oral cannabinoid compositions of embodiment 1, which comprises about 5% (w/w) of the cannabinoid.
10. The oral cannabinoid compositions of embodiment 1, which comprises about 6% (w/w) of the cannabinoid.
11. The oral cannabinoid compositions of embodiment 1, which comprises about 7% (w/w) of the cannabinoid.
12. The oral cannabinoid compositions of embodiment 1, which comprises about 8% (w/w) of the cannabinoid.
13. The oral cannabinoid compositions of embodiment 1, which comprises about 9% (w/w) of the cannabinoid.
14. The oral cannabinoid compositions of embodiment 1, which comprises about 10% (w/w) of the cannabinoid.
15. The oral cannabinoid compositions of any one of the embodiments 1 to 14, wherein the cannabinoid is cannabidiol (CBD), cannabidiolic acid (CBDA), cannabidivarin (CBDV), cannabigerol (CBG), cannabigervarin (CBGV), tetrahydrocannabivarin (THCV), tetrahydrocannabinol (THC) or any combination thereof.
16. The oral cannabinoid compositions of embodiment 15, wherein the cannabinoid is cannabidiol (CBD).
17. The oral cannabinoid compositions of any one of the embodiments 1 to 16, which comprises about 40% (w/w) of the surfactant.
18. The oral cannabinoid compositions of any one of the embodiments 1 to 16, which comprises about 41% (w/w) of the surfactant.
19. The oral cannabinoid compositions of any one of the embodiments 1 to 16, which comprises about 42% (w/w) of the surfactant.
20. The oral cannabinoid compositions of any one of the embodiments 1 to 16, which comprises about 43% (w/w) of the surfactant.
21. The oral cannabinoid compositions of any one of the embodiments 1 to 16, which comprises about 44% (w/w) of the surfactant.
22. The oral cannabinoid compositions of any one of the embodiments 1 to 16, which comprises about 45% (w/w) of the surfactant.
23. The oral cannabinoid compositions of any one of the embodiments 1 to 16, which comprises about 46% (w/w) of the surfactant.
24. The oral cannabinoid compositions of any one of the embodiments 1 to 16, which comprises about 47% (w/w) of the surfactant.
25. The oral cannabinoid compositions of any one of the embodiments 1 to 16, which comprises about 48% (w/w) of the surfactant.
26. The oral cannabinoid compositions of any one of the embodiments 1 to 16, which comprises about 49% (w/w) of the surfactant.
27. The oral cannabinoid compositions of any one of the embodiments 1 to 16, which comprises about 50% (w/w) of the surfactant.
28. The oral cannabinoid compositions of any one of the embodiments 1 to 27, wherein the surfactant is an ethoxylated fatty alcohol, polyethylene glycol (PEG)-1000 monocetyl ether, alkyl trimethyl ammonium bromide, glycerol monostearate, potassium stearate, sodium lauryl sulphate, sodium cetearyl sulphate, saponin, Polysorbate 20 (Tween 20), Polysorbate 40 (Tween 40), Polysorbate 60 (Tween 60) and Polysorbate 80 (Tween 80) or any combination thereof.
29. The oral cannabinoid compositions of embodiment 28, wherein the surfactant is Polysorbate 60 (Tween-60) or Polysorbate 80 (Tween-80).
30. The oral cannabinoid compositions of any one of the embodiments 1 to 29, which comprises about 15% (w/w) of oil or semi-solid fat.
31. The oral cannabinoid compositions of any one of the embodiments 1 to 29, which comprises about 16% (w/w) of oil or semi-solid fat.
32. The oral cannabinoid compositions of any one of the embodiments 1 to 29, which comprises about 17% (w/w) of oil or semi-solid fat.
33. The oral cannabinoid compositions of any one of the embodiments 1 to 29, which comprises about 18% (w/w) of oil or semi-solid fat.
34. The oral cannabinoid compositions of any one of the embodiments 1 to 29, which comprises about 19% (w/w) of oil or semi-solid fat.
35. The oral cannabinoid compositions of any one of the embodiments 1 to 29, which comprises about 20% (w/w) of oil or semi-solid fat.
36. The oral cannabinoid compositions of any one of the embodiments 1 to 29, which comprises about 21% (w/w) of oil or semi-solid fat.
37. The oral cannabinoid compositions of any one of the embodiments 1 to 29, which comprises about 22% (w/w) of oil or semi-solid fat.
38. The oral cannabinoid compositions of any one of the embodiments 1 to 29, which comprises about 23% (w/w) of oil or semi-solid fat.
39. The oral cannabinoid compositions of any one of the embodiments 1 to 29, which comprises about 24% (w/w) of oil or semi-solid fat.
40. The oral cannabinoid compositions of any one of the embodiments 1 to 29, which comprises about 25% (w/w) of oil or semi-solid fat.
41. The oral cannabinoid compositions of any one of the embodiments 1 to 40, wherein one or more oil or semi-solid fat are soybean oil, olive oil, fish oil, fish oil extract, safflower oil, corn oil, sunflower oil, coconut oil, palm kernel oil, rapeseed oil, sesame oil, vegetable oils, mineral oils, medium chain triglycerides (MCT) and mixtures thereof.

42. The oral cannabinoid compositions of embodiment 41, wherein one or more oil or semi-solid fat is medium chain triglyceride (MCT) oil extracted from coconut oil.

43. The oral cannabinoid compositions of any one of the embodiments 1 to 42, which comprises about 25% of the co-solvent.

44. The oral cannabinoid compositions of any one of the embodiments 1 to 42, which comprises about 26% of the co-solvent.

45. The oral cannabinoid compositions of any one of the embodiments 1 to 42, which comprises about 27% of the co-solvent.

46. The oral cannabinoid compositions of any one of the embodiments 1 to 42, which comprises about 28% of the co-solvent.

47. The oral cannabinoid compositions of any one of the embodiments 1 to 42, which comprises about 29% of the co-solvent.

48. The oral cannabinoid compositions of any one of the embodiments 1 to 42, which comprises about 30% of the co-solvent.

49. The oral cannabinoid compositions of any one of the embodiments 1 to 42, which comprises about 31% of the co-solvent.

50. The oral cannabinoid compositions of any one of the embodiments 1 to 42, which comprises about 32% of the co-solvent.

51. The oral cannabinoid compositions of any one of the embodiments 1 to 42, which comprises about 33% of the co-solvent.

52. The oral cannabinoid compositions of any one of the embodiments 1 to 42, which comprises about 34% of the co-solvent.

53. The oral cannabinoid compositions of any one of the embodiments 1 to 42, which comprises about 35% of the co-solvent.

54. The oral cannabinoid compositions of any one of the embodiments 1 to 53, wherein the co-solvent is diethylene glycol ethyl ether, methoxy polyethylene glycol, propylene glycol, polypropylene glycol, polyethylene glycol (PEG), glycerol, ethanol, dimethyl isosorbide, glycofurol propylene carbonate, dimethyl acetamide, combinations or mixtures thereof.

55. The oral cannabinoid compositions of any one of the embodiments from 43 to 54, wherein the co-solvent has a mean molecular weight in the range from 100 to 20000 Da.

56. The oral cannabinoid compositions of any one of the embodiments 54 or 55, wherein the co-solvent is PEG 2000, PEG 5000, PEG 10000 or PEG 20000.

57. The oral cannabinoid compositions of any one of the embodiments 1 to 56, wherein the compositions are emulsion pre-concentrates at the time of administration.

58. The oral cannabinoid compositions of embodiment 57, wherein the emulsion pre-concentrate may be filled into single unit dosage forms such as capsules, drinking ampoules and dose cushions, or may alternatively be formed as other suitable dosage forms such as powder, granules, pellets, chewable soft pills and chewy-base lozenges.

59. The oral cannabinoid compositions of any one of the embodiments 57 or 58, wherein the compositions are self-emulsifying capsules.

60. The oral cannabinoid compositions of any one of the embodiments 1 to 59, wherein the compositions remain stable for 2-3 months from 0 to 40° C.

61. The oral cannabinoid compositions of any one of the embodiments 1 to 60, wherein the compositions have 10 times more absorption rate as compared to controls.

62. The oral cannabinoid compositions of embodiment 61, wherein the compositions have strong bioavailability profile in in-vivo models with peak plasma levels of >1000 ng/ml at 1 hour.

63. The oral cannabinoid compositions of any one of the embodiments 1 to 62, wherein the compositions dispersed into nanosized droplets in 30 minutes to 2 hours time.

64. The oral cannabinoid compositions of embodiment 63, wherein the compositions have droplet size of 30 to 400 nm as determined by dynamic light scattering.

65. The oral cannabinoid compositions of any one of embodiments 1 to 64, wherein the compositions form in-situ oil-in-water emulsion upon contact with aqueous media such as gastrointestinal fluids.

66. The method comprising administering the oral cannabinoid compositions of any one of embodiments 1 to 65 to a subject for the treatment of neuropathic pain condition.

67. The method of embodiment 66, wherein the neuropathic pain is caused by alcoholism; amputation; cancer; carpal tunnel syndrome; chemotherapy; diabetes; facial nerve problems; HIV infection/AIDS; multiple myeloma; multiple sclerosis; nerve or spinal cord compression from herniated discs or from arthritis in the spine; shingles; spine surgery; syphilis; thyroid problems or vitamin B deficiency.

68. The method of any one of embodiments 66 or 67, wherein the subject is a mammal.

69. The method of any one of embodiments 66 to 68, wherein the subject is a companion animal.

70. The method of embodiment 68, wherein the subject is a human.

71. The method of any one of embodiments 66 to 70, wherein the method further comprises administering an additional therapy for neuropathic pain to a subject.

72. Use of the oral cannabinoid compositions of any one of the embodiments 1 to 65 for the treatment of neuropathic pain in a subject.

73. The use of embodiment 72, wherein the neuropathic pain is caused by alcoholism; amputation; cancer; carpal tunnel syndrome; chemotherapy; diabetes; facial nerve problems; HIV infection/AIDS; multiple myeloma; multiple sclerosis; nerve or spinal cord compression from herniated discs or from arthritis in the spine; shingles; spine surgery; syphilis; thyroid problems or vitamin B deficiency.

74. The use of any one of embodiments 72 or 73, wherein the subject is a mammal.

75. The use of any one of embodiments 72 to 74, wherein the subject is a companion animal.

76. The use of embodiment 74, wherein the subject is a human.

77. The use of any one of embodiments 72 to 76, wherein the treatment further comprises an additional therapy for neuropathic pain.

NON-LIMITING EXAMPLES

The discussion herein and the following Examples set forth and illustrate various exemplary embodiments of the present disclosure, which are understood to be illustrative and non-limiting.

Example 1

Following oral cannabinoid SEDDS compositions were formulated by altering the molecular weight of co-solvent polyethylene glycol (PEG):

TABLE 1

| SEDDS compositions: | | | | |
|---|---|---|---|---|
| Formulation 1 | Formulation 2 | Formulation 3 | Formulation 4 | % w/w |
| CBD | CBD | CBD | CBD | 5.0 |
| Tween-60/ Tween-80 | Tween-60/ Tween-80 | Tween-60/ Tween-80 | Tween-60/ Tween-80 | 45.0 |
| MCT Oil | MCT Oil | MCT Oil | MCT Oil | 20.0 |
| PEG 2000 | PEG 5000 | PEG 10000 | PEG 20000 | 30.0 |

Example 2

The following procedure was used to produce a laboratory batch of each SEDDS formulation according to the formulas in Table 1:
a) in an appropriate vial (8 mL or 20 mL), add polyethylene glycol, Tween-60 or Tween-80 (melted) and MCT oil.
b) Weigh CBD on wax paper and add to the mixture.
c) Add >95% ethanol to the mixture.
d) Seal the mixture with appropriate lid.
e) Using an appropriate heating system, warm up (≈70-80° C.) the loaded vials (well-sealed) and vortex. Repeat the steps until full dissolution and homogenous mixture is obtained.
f) Using Rota-vapor, run evaporation of ethanol from the mixture and keep the water bath at 60-70° C.
g) Keep the vials at ≈60° C. in a water bath until the full evaporation of ethanol is done.
h) Weight empty capsules and record the weight.
i) Open the capsules and put on a tray the bottom of the capsules (longer part).
j) Using syringe (pre warm at 30-40° C.), fill the capsules from top with the hot mixture.
k) Wait at least 20 minutes until the mixture solidifies in the capsules and close the capsules.
l) To accelerate the solidification of mixture in the capsules apply the cold refrigerated conditions using ice (for lab-scale production) or cold air flow for large scale production.

Figure 1:
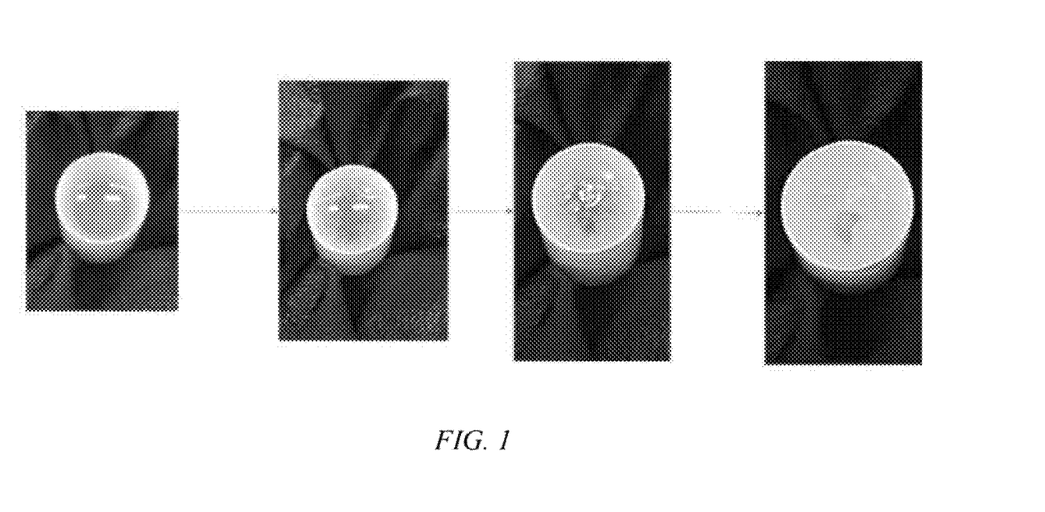
FIG. 1 illustrates loaded warm self-emulsifying mixture within the SEDDS capsules, according to example embodiments.
Figure 2:
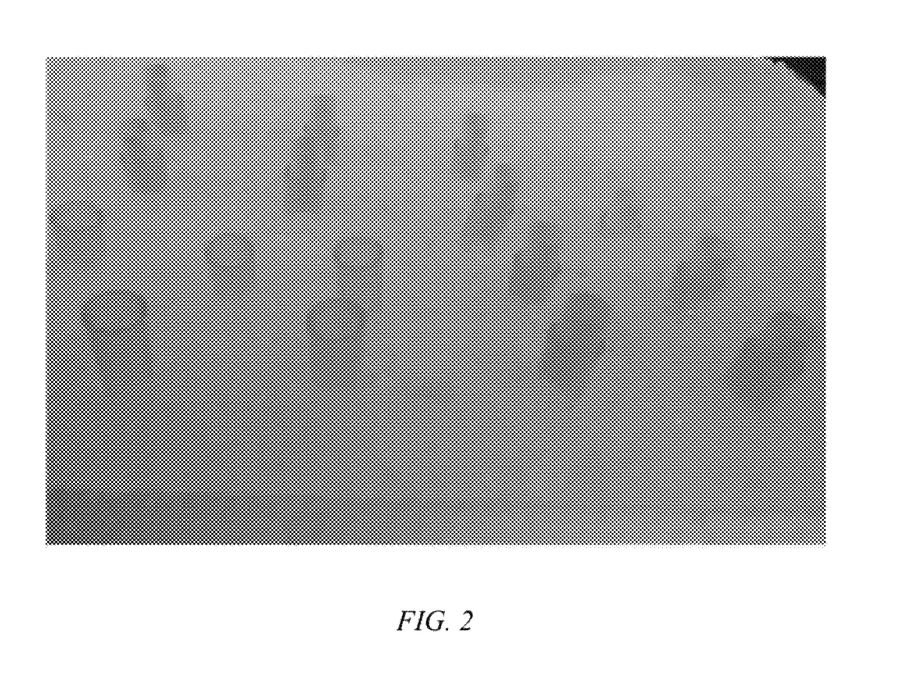
FIG. 2 illustrates solidification of loaded capsules under cold conditions, pipette tips were sealed at the bottom and placed on ice to avoid condensation within the tips, according to example embodiments.

FIG. 1 illustrates warm mixture of ingredients at 60-70° C. in capsules & FIG. 2 illustrates solidification of loaded capsules under cold conditions, pipette tips were sealed at the bottom and placed on ice to avoid condensation within the tips.

Example 3

Figure 3:
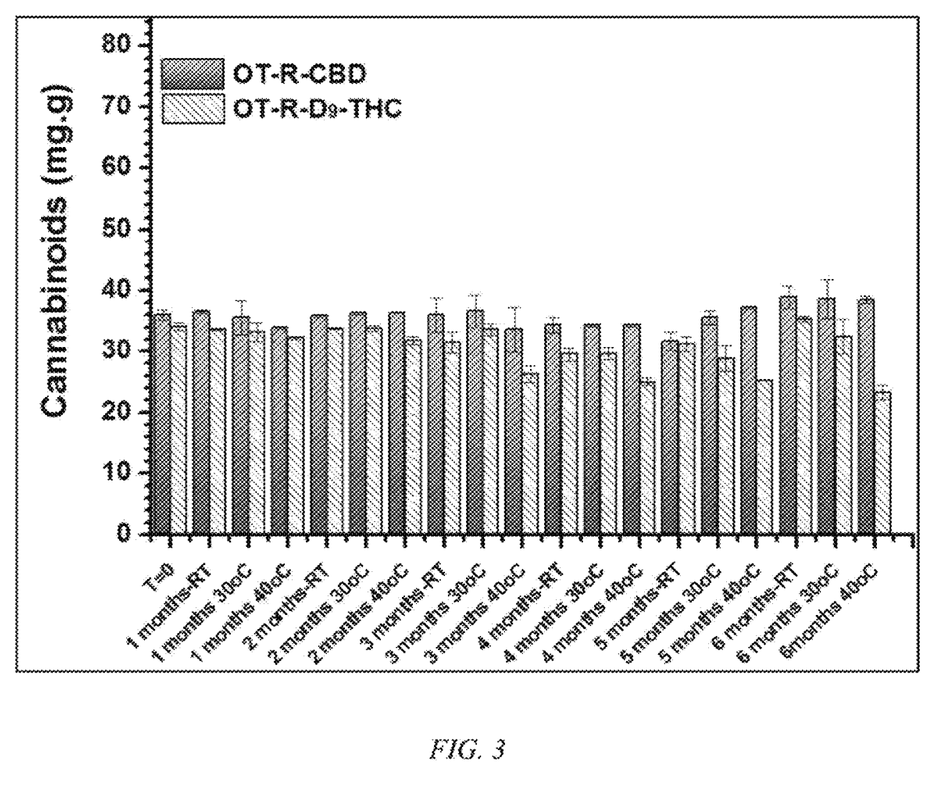
FIG. 3 illustrates stability results of cannabinoids by HPLC at room temperature (RT), 30° C. and 40° C. under dark conditions at 0, 10 and 40-day time points, according to example embodiments.

Assessment of stability—Formulations were analysed for cannabinoid concentrations using High Performance Liquid Chromatography (HPLC) method. Test samples were stored at 4° C. and 40° C. under dark conditions. Tetrahydrocannabinol (THC) capsules were prepared as per methods described in Example 2 and were used as controls. Samples were analysed by HPLC at 0, 10 and 40-day time points. Samples of formulations taken within the capsules have demonstrated good stability with no apparent degradation. CBD remains stable over 40-day incubation at 40° C. in the formulations whereas THC degrades significantly. FIG. 3 illustrates stability results of cannabinoids by HPLC at room temperature (RT), 30° C. and 40° C. under dark conditions at 0, 10 and 40-day time points.

Example 4

Assessment of Bioavailability

Methods

Pharmacokinetic study was performed to assess the bioavailability of SEDDS formulations in animal models. Female Sprague-Dawley rats (n=13) were administered 19.3 mg/kg of CBD via gavage as either CBD in SEDDS formulation (Test); MCT-CBD isolate (Control 1) or MCT-CBD resin (Control 2). Blood was collected at 1, 2, 4, 6, 8, 10- and 24-hours post administration. CBD was extracted from plasma prior to analysis of CBD concentrations via Liquid chromatography-mass spectrometry (LC-MS) method.

Cannabinoid Quantification

Reagents and chemicals: CBD was purchased from Restek Corporation (Bellfornte, PA). Working calibration standards were prepared in acetonitrile. Trifluoroacetic acid (TFA) was obtained from Sigma Aldrich. Acetonitrile (HPLC grade) was obtained from Caledon Laboratories.

Instrumentation

Analysis was performed using an Agilent 1260 Infinity II (Agilent Technologies, Santa Clara, CA) system equipped with a quaternary pump, autosampler, thermos column compartment and UV DAD detector. Chemstation software was used to control the instrument components and acquire, store, and analyze UV data. Tandem mass spectrometry was performed using a TSQ Endura™ Triple Quadrupole Mass Spectrometer (Thermo Fisher Scientific, Waltham, MA) operating in electrospray ionization (ESI). Xcalibur software (Thermo Fisher Scientific) was used for instrument control, data acquisition, qualitative and quantitative data analyses. Cannabinoid standards (using a previously extracted CBD isolate) were prepared in methanol from a concentration range between 5-250 ng/mL. The MS conditions were set as follows: the flow rate of sheath gas, aux gas, and sweep gas were kept at 2.42 arb, 7.31 arb, and 5.69 arb, respectively. Ion transfer tube and vaporizer temperatures were set to 275° C. and 400° C. respectively.

CBD Analysis In-Vitro

The mobile phases consisted of 20% distilled water, 0.1% TFA (mobile phase A) and 80% acetonitrile 0.1% TFA (v/v) (mobile phase B). Flow rate used was 1 ml·min$^{-1}$ and runtime per analysis was setup at 14 min. Injection of standards and samples was setup at 20 µl. The column chosen for CBD analysis was from Waters, Xterra $C_{18}$ 4.6×250 mm×5.0 µm and a guard column Xterra. CBD was detected at 6.4 min and THC at 11.3 min (+/−0.1 min) using UV-DAD set at 220 nm.

CBD Analysis In-Vivo

Plasma Extraction. 20 µL of plasma was added to a 1:1 (v/v) solution of acetonitrile:ethyl acetate at a ratio of 1:10 (plasma:organic solvent). Samples were vortexed for 30 seconds. Following this, samples were centrifuged at 1×10⁴ RCF at 10° C. for 20 minutes. Following this the supernatant was collected and transferred to a fresh 2 mL tube. The supernatant was evaporated under nitrogen at 37° C. The samples were reconstituted with LC-MS grade methanol prior to analysis by mass spectrometry.

Sample Analysis was performed on an Agilent Poroshell 120 C18 column (150×2.1 mm; 1.9 μm particle size). The mobile phase was composed of (A) water w/0.1% (v/v) formic acid (FA) and (B) Acetonitrile w/0.1% (v/v) FA at a ratio of 20:80 respectively. The flow rate was 0.2 mL/min and the column temperature was maintained at 40° C. The injection volume was 5 μL and the injector needle was washed with methanol and the autosampler was maintained at room temperature.

Results

Figure 4:
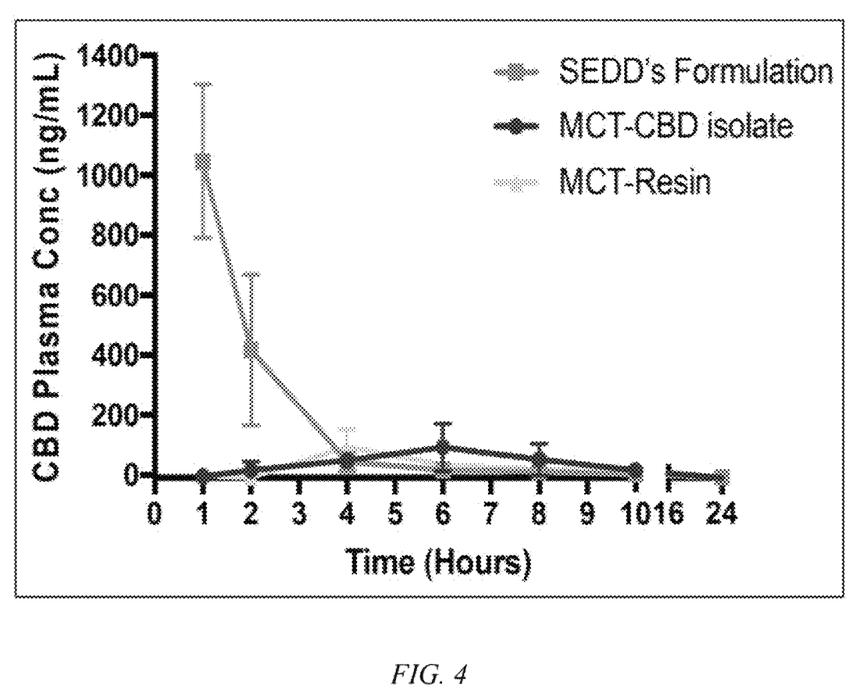
FIG. 4 illustrates CBD Plasma Concentration for MCT-CBD isolate (Control 1) vs. MCT-CBD resin (Control 2) vs. SEDDS formulations (Test), according to example embodiments.

Compared to the controls, SEDDS formulation achieved rapid absorption with peak plasma levels of >1000 ng/mL at 1 hour. Control formulations showed peak plasma concentrations of approximately 90 ng/mL at 4-6 hours. At similar dose, peak plasma of CBD was 10 times higher than the controls (FIG. 4).

TABLE 2

CBD Plasma Concentration for MCT-CBD isolate (Control 1) vs. MCT-CBD Resin (Control 2) vs. SEDDS Formulations (Test).

| Sample | Peak plasma conc. (ng/ml) | Peak time (Hours) |
|---|---|---|
| MCT-CBD isolate (Control 1) | 91.98 | 6 hours |
| MCT-CBD Resin (Control 2) | 93.10 | 4 hours |
| SEDDS Formulations (Test) | 1046.99 | 1 hour |

Example 5

Figure 5:
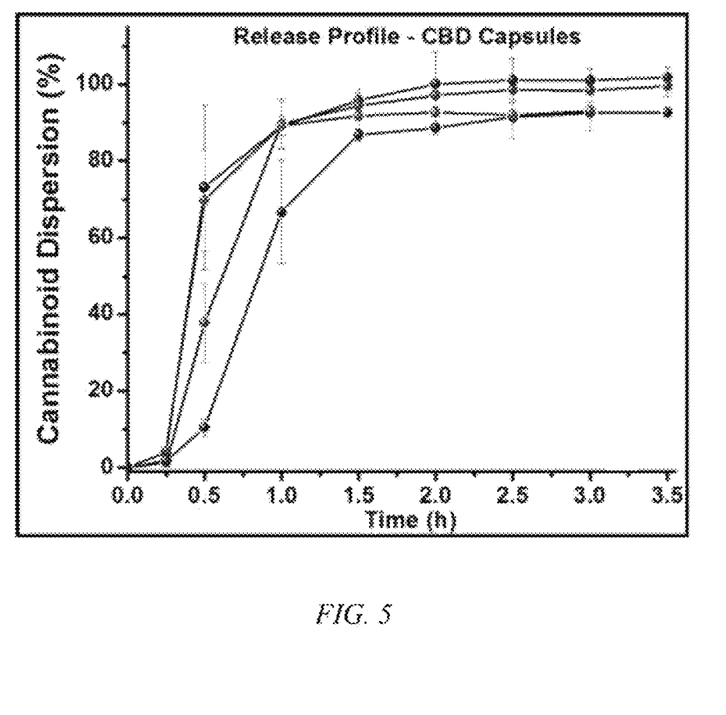
FIG. 5 illustrates dispersion profile of CBD loaded capsules at 1, 2- and 3-hour time points, according to example embodiments.

Assessment of dissolution—Test samples of each of the candidate formulations were evaluated in a Distek Premier 5100 dissolution apparatus using USP 711 method for fast dispersion. Similar dispersion profile was observed for CBD loaded capsules (FIG. 5). In less than 1.5 hours, cannabinoids were dispersed in PBS pH 7.4 in nanocarriers. Determined by dynamic light scattering, size of the droplets loaded with cannabinoid was estimated 40±5 nm.

While the foregoing has presented specific embodiments of the present disclosure, it is to be understood that these embodiments have been presented by way of example only. It is expected that others skilled in the art will perceive variations which, while varying from the foregoing, do not depart from the spirit and scope of the disclosure herein.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this disclosure belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the disclosure herein.

The invention claimed is:

1. A self-emulsifying oral composition comprising a cannabinoid consisting of cannabidiol (CBD) at 0.01-10% (w/w), polysorbate 80 at 40-50% (w/w), medium chain triglycerides (MCI) extracted from coconut oil at 15-25% (w/w), and polyethylene glycol (PEG) 2000, PEG 5000, PEG 10000 or PEG 20000 at 25-35% (w/w), wherein the said composition forms an in-situ oil-in-water emulsion upon contact with aqueous media.

2. The oral cannabinoid composition of claim 1, wherein the composition is an emulsion pre-concentrate.

3. The oral cannabinoid composition of claim 2, wherein the emulsion pre-concentrate is filled into single unit dosage forms selected from self-emulsifying capsules, drinking ampoules, dose cushions, or any other suitable dosage forms selected from powder, granules, pellets, chewable soft pills and chewy-base lozenges.

4. The oral cannabinoid composition of claim 3, wherein the composition is a self-emulsifying capsule.

5. The oral cannabinoid composition of 1, wherein the composition is formulated to achieve in-vivo peak plasma levels in the range of 900 to 1100 ng/ml at 1 hour.

6. A method of treating a neuropathic pain condition in a subject caused by alcoholism; amputation; cancer; carpal tunnel syndrome; chemotherapy; diabetes; facial nerve problems; HIV infection/AIDS; multiple myeloma; multiple sclerosis; nerve or spinal cord compression from herniated discs or from arthritis in the spine; shingles; spine surgery; syphilis; thyroid problems or vitamin B deficiency comprising administering to the subject an oral composition of claim 1.

7. The composition of claim 1 comprising a cannabinoid consisting of cannabidiol (CBD) at about 5% (w/w), polysorbate 80 at about 45% (w/w), medium chain triglycerides (MCT) extracted from coconut oil at about 20% (w/w), and a polyethylene glycol (PEG) 2000, PEG 5000, PEG 10000 or PEG 20000 at about 30% (w/w), wherein the said composition forms in-situ oil-in-water emulsion upon contact with aqueous media.

\* \* \* \* \*